United States Patent
Watson et al.

(10) Patent No.: US 6,939,829 B1
(45) Date of Patent: Sep. 6, 2005

(54) PLANT AND PRODUCT TREATMENT

(76) Inventors: Robert John Watson, 73 Stintons Rd., Park Orchards, 3114 Victoria (AU); Henry Joseph Kotula, 5 Maitland Rise, Woodvale, 6026, Western Australia (AU); Matthew Lenno Gooding, 1689 S. Country Rd. 15, Tiffin, OH (US) 44883

( * ) Notice: Subject to any disclaimer, the term of this patent is extended or adjusted under 35 U.S.C. 154(b) by 0 days.

(21) Appl. No.: 10/070,224

(22) PCT Filed: Aug. 25, 2000

(86) PCT No.: PCT/AU00/01009

§ 371 (c)(1),
(2), (4) Date: Dec. 23, 2002

(87) PCT Pub. No.: WO01/15536

PCT Pub. Date: Mar. 8, 2001

(30) Foreign Application Priority Data

Aug. 27, 1999 (AU) .............................................. PQ2483

(51) Int. Cl.⁷ .............................................. A01N 37/00
(52) U.S. Cl. ...................................... 504/142; 514/558
(58) Field of Search .......................... 514/558; 504/142

(56) References Cited

U.S. PATENT DOCUMENTS 5,425,952 A * 6/1995 Winston ...................... 424/717

FOREIGN PATENT DOCUMENTS

| AU | 59941/90 | * | 1/1991 |
| AU | A-59941/90 | | 1/1991 |
| IL | 105109/3 | | 6/1996 |
| JP | 59071387 | * | 4/1984 |

OTHER PUBLICATIONS

Rakieten et al, Comparison of constituents in orange juice, 1951, J. Am. Dietet. Assoc., vol. 27. pp. 864–868.*

Arena, M. E., et al., "Inhibition of Growth of *Lactobacillus Plantarum* Isolated from Citrus Fruits in the Presence of Organic Acids," *Microbiologie*, vol. 14 at pp. 219–226 (1996).

Don–Pedro, Kio N., Investigation of Single and Joint Fumigant Insecticidal Action of Citruspeel oil Components, *Pestic. Sci.*, vol. 46 at pp. 79–84 (1996).

* cited by examiner

*Primary Examiner*—Alton Pryor
(74) *Attorney, Agent, or Firm*—Edwin D. Schindler

(57) ABSTRACT

A mixture of a citrus agent which contains, for example, a bioflavenoid, and caprylic acid acts synergistically to treat plants by providing anti-bacterial and anti-fungal protection to plants. In a preferred embodiment, a micro-nutrient is added to the mixture to simulate plant growth, while continuing to provide the stated protection to plants.

9 Claims, No Drawings

PLANT AND PRODUCT TREATMENT

BACKGROUND OF THE INVENTION

1. Technical Field of the Invention

This invention relates to a plant and product treatment and in particular to a treatment which acts as an anti-mildew and antifungal spray which also has anti-bacterial properties. The invention also provides, in association with such treatment a synergistic treatment which encourages growth of plants.

2. Description of the Prior Art

Historically, plants and crops (hereinafter generally referred to as plants) have been treated by the use of traditional agri-chemicals many, of which have been found to have undesirable side-effects. As a result, there has been pressure, mainly from consumers, for a move towards safer and more "natural based" alternatives. This can be attributed to;

A growing global trend towards the reduction of chemical and pesticide use

A push for more "Organic Produce"

Growing public concern's over what goes into our food

The introduction of tougher legislation either banning or severely restricting the use of many existing chemicals Growing public awareness to the effects of prolonged exposure or use of chemicals In Europe, for example, Government's are providing incentives to growers who adopt more desirable practices. This new approach, which is established on a country by country basis, is essentially a move as close as possible towards total organic production.

It is known to use, as an anti-bacterial agent, products produced from citrus, specifically oranges, such as a product called Cytrosan (Trade Mark but there are other broadly similar products such as Citrex (Trade Mark)) and which can be considered to be a mixture of bioflavanoids or products made from different citrus fruit such as grapefruit. For convenience, we shall refer to these types of products as citrus agents.

Citrus agents are conventionally made from the residue of juice manufacture, skin, pulp and pips, and this residue is dried and then ground into a powder. If required, the product can be treated to remove the soluble material, largely the bioflavanoids, therefrom leaving the fibre as waste. The treatment to remove the soluble material may be by the use of glycerine in which the bioflavanoids are soluble.

Caprylic acid (which is also known as octanoic acid) is known as an anti-fungal agent.

Both the citrus agents and caprylic acid are quite expensive.

SUMMARY OF THE INVENTION

The object of the invention is to provide a new plant and product treatment which has anti-bacterial and anti-fungal actions which have not been achieved by either citrus agents or caprylic acid and which can also preferably have anti-mildew and anti-viral properties.

We have found that the provision of a mixture of citrus agent and caprylic acid together with carriers, possibly alcohol, surfactant and water, provides a synergistic mixture which gives a better result than the use of either of the compounds alone when used to treat plant materials and plant products.

We have also found that when such a mixture is combined with a micro-nutrient (the use of which is known to assist in plant growth), the growth of plants is substantially enhanced over what would have been expected from each of the treatments alone.

DETAILED DESCRIPTION OF THE PREFERRED EMBODIMENTS

In a first aspect, the invention thus includes a synergistic mixture for the treatment of plant and plant products which includes both a citrus agent and caprylic acid.

We have found by using a mixture of the invention we can reduce considerably the quantity of citrus agent needed to give a required end result and use only a small quantity of caprylic acid, which is also expensive, to provide a treatment which is very much cheaper than previously available using these compounds separately to provide the results required.

In a second aspect of the invention, we add to the mixture as described above, a micro-nutrient.

The micro-nutrient may come from the class of materials known as NPK's, substances which are a mixture of nitrogen, phosphorus and potassium together with trace elements.

The invention also includes a method of treating plants against bacteria and fungus by spraying these at least once during the growing season with the mixture of a citrus agent and caprylic acid.

Also included in the invention is such a method wherein a micro-nutrient is added to or sprayed with the mixture.

In order that the invention may be more readily understood we shall describe particular embodiments of the invention.

In the first embodiment we use a mixture formed as follows:

| | |
|---|---|
| citrus agent | 30–60% |
| caprylic acid | 10–30% |
| alcohol | 10–30% |
| surfactant | 5–15% |

In a specific mixture which we have used and from which we have had very good results, we use:

| | |
|---|---|
| Cytrosan (a specific citrus agent) | 44.4% |
| caprylic acid | 22.2% |
| alcohol | 22.2% |
| surfactant | 11.1% |

This product we refer to as Croplife.

The mixture for use is diluted and we have found that when it is required for use against Downey and Powdery mildew the dilution can be very high. We have found that between 0.25 and 15 ml per liter of the mixture added to make up 100 litres provides a satisfactory dilution and 500 litres of this mixture provides good coverage for one hectare.

For golf course fungi we have found a dose rate of one litre of the mixture in 100 liters of water, 10 ml/liter, is satisfactory.

For fungi found during mushroom production we use a mixture of 3–4 ml per liter of water.

We have effected field trials in mushrooms, grapes, grasses, apples pears mangos potatoes and tomatoes, all with effective results.

We have found that we have had positive results against three specific fungi, *Verticilliun fungicola* var. *fungicola* (dry bulb), *Mycogone perniciosa* (wet bulb) and *Cladobotrywn dendroides*, formally "*Dactylium dendroides*" (Cobweb), which have developed a mutagenic resistence to conventional fungicides.

The synergistic mixture of the invention satisfactorily killed these fungi.

In the vineyards we used the product again the fungus Botrytus (*Botrytis cinerea*) and the mildews, Downey Mildew (*Plasmopara viticola*) and Powdery mildew (*Uncinulanecator*) and the product has been successful against these.

The product has been used in grasses and has successfully been used against the following fungi:
*Fusarium acuminaturi*
Brown Spot (*Rhizoctonia*)
Dollar Spot (*Sclerotonia homoeocarpa*)
Fairy Ring (*Agraricales & Gastromycelae*).
Tests against bacteria have also provided satisfactory results and amongst bacterias tested are:
Pseudomonas
Erwinia
Anthracnose These tests have also shown that the product appears to be a systemic, that is that a certain percentage of the product will be taken up by the plant through both the leaves and roots and its effectiveness will be retained for some time.

Not only have we tried the product on the plants and fruit whilst being grown, we also found that the product can also be valuable post-harvest by dipping or spraying the product into a diluted mixture of the product and this has assisted the life of the harvested products. Where the product has been treated in the field before being treated post-harvest, the results have been enhanced.

Practically, we prefer that the product be applied to plants during the cool of the day, and preferably not prior to or just subsequent to rain. As the product is taken up by the leaves, it is better, if it is likely to rain within six hours to apply the product at a later time.

Also, we have found that to obtain best results, the product can be sprayed in a light mist and the spray be repeated some five days after the first spray.

If, after a second spray, there is still signs of the infestation, the spraying can be repeated after a further five days.

We have found that the residues of the product components are not toxic, they are applied in only small quantities, both the citrus agent and the caprylic acid are natural products which are acceptable for use in food and, in any case, because of the low concentrations, the amount of residues is extremely small.

Whilst in the specification we have described particular certain applications and percentages of components and quantities applied, it is to be understood that these are exemptary of the invention and not restrictive.

The invention provides a treatment which is cheaper than using high percentage citrus agent as, because of the synergistic effect of the citrus agent and the caprylic acid, the quantity of citrus agent used is greatly reduced and whilst caprylic acid is itself quite expensive, it is used in such small quantities that the overall cost is minimised. There can be changes in the specific citric agent, the alcohol and the surrfactant and where such changes are made, the proportions may have to be varied based on empirical information.

In the second aspect of the invention, we use the product described above together with a micro-nutrient (or nutritional solution).

These micro-nuirients themselves are known and one particular form "Growers" is an NPK product which includes nitrogen, phosphorus and potassium in a 10:20:10 ratio, together with a large number of trace elements. Growers and similar products are known as nutritional solutions. Whilst in the specific examples, we will refer to the use of Growers, it is to be understood that ihis is an exemplification of a class of known products.

The ratio of the two components can be varied depending on the particular application but, generally we suggest between 5 to 20 ml of Croplife to 1 liter of Growers but these proportions are not limiting.

Some qualitative results of the use of the mixture are as follows:

Apples and Pears—DONNYBROOK
  Treated 1 hectare of Packham Pears and 1 Hectare of Royal Gala Apples with three treatments of Croplife and two treatments Growers Spray. Pears from the crop were stored in CA for 6 months with conventional DPA treatment. Product had very little rot and mould.
Potatoes—Ohio USA
  Application rate 4 liter Growers/60 ml Croplife per acre applied 6 times during season. Resulted in:
  Better Sustained Growth.
  No disease outbreaks.
  Much improved yield.
Tomatoes
  This grower was able to compare the trial plot which comprised 4 acres against a traditionally treated plot and neighbouring plots.
  Application Rate 4 liters Growers+90 ml Croplife per acre applied 4 times in season. Resulted in;
  Reduction in traditional fungicides and fumigants.
  Reduction in fertiliser used.
  Reduction in disease (fungi).
  Better product size.
  Grower said advantage in using Croplife/Growers amounted to saving of USD550/acre over traditional farming with crop as good if not better.
  Surrounding blocks under disease pressure.
Tomatoes—Greenhouse
  Application rate of 2 tablespoons Growers+¼ oz (7.5 mls) Croplife per 4 liters of water applied weekly. Resulted in;
  Significant reduction in incidence of disease.
  Better sized and greater volume of produce.
Capsicum
  Application rate of 4 liters Growers+90 ml Croplife/Acre applied four times per season.
  Significant reduction in incidence of disease.
  Better sustained crop.
  Better yield.
Ornamentals—Mum's
  Application rate of 2 Tablespoons Growers+¼ oz (7.5ms) Croplife per 4 liters of water weekly.
  Plants were essentially disease free.
  Much better visible sustained growth.
  Superior plant.
Soybean
  Application rate of 6 liters Growers+60 ml Croplife/Acre every 2 weeks after plants were over 6" tall.

Plants were shooting more suckers.
Generally healthier.
Crop loaded.

Grapes

Application rate of 4 Liters Growers+60 ml Croplife/Acre applied 4 times during season. Resulted in:

Significant disease reduction.
Healthier looking plant and product.
Expect yield increase will follow.

Wheat

Application rate of 12 liters Growers+6 ml Croplife per acre 3 times during season. Resulted in;

Dramatic yield increase of 13.5 Bushells/acre.

Strawberries

Used as a transplant solution of 60 mls Growers+30 ml Croplife per gallon with much improved transplant rate and noticeably more vigorous growth.

It can be seen from these results that, generally, not only were the plants healthier than would otherwise be the case but, also, all forms of infestation, bacterial and fungal appear to be controlled better than by the use of any of the components separately and the final plant was better and stronger than would have been expected to be the case using more conventional agri-chemicals.

We claim:

1. A synergistic mixture for treating plant and plant products, comprising:

| | |
|---|---|
| a citrus agent | 30%–60% |
| caprylic acid | 10%–30% |
| an alcohol | 10%–30% |
| a surfactant | 5%–15%. |

2. The synergistic mixture according to claim 1, where said citrus agent is cytrosan, and said mixture comprises:

| | |
|---|---|
| a citrus agent | 44.4% |
| caprylic acid | 22.2% |
| an alcohol | 22.2% |
| a surfactant | 11.1%. |

3. The synergistic mixture according to claim 1, wherein said mixture is in a spray form.

4. The synergistic mixture according to claim 3, wherein said spray form is diluted with 0.25 ml to 1.5 mil per liter of water.

5. The synergistic mixture according to claim 1, further comprising an NPK as a micro-nutrient, said NPK comprising up to 45% of said synergistic mixture.

6. The synergistic mixture according to claim 5, wherein said NPK is a mixture of nitrogen, phosphorous, potassium and trace elements.

7. The synergistic mixture according to claim 6, wherein said nitrogen, phosphorus and potassium are in a ratio of 10:20:10.

8. The synergistic mixture according to claim 5, wherein said mixture is in a spray form.

9. The synergistic mixture according to claim 8, wherein said spray form is diluted with 0.25 ml to 1.5 mil per liter of water.

\* \* \* \* \*